United States Patent [19]

Schulenberg

[11] 4,244,954

[45] Jan. 13, 1981

[54] ACRIDINE COMPOUNDS AND METHODS OF COMBATTING VIRUSES WITH THEM

[75] Inventor: John W. Schulenberg, Rensselaer, N.Y.

[73] Assignee: Sterling Drug Inc., New York, N.Y.

[21] Appl. No.: 947,715

[22] Filed: Oct. 2, 1978

Related U.S. Application Data

[63] Continuation-in-part of Ser. No. 774,399, Mar. 4, 1977, Pat. No. 4,150,134, which is a continuation-in-part of Ser. No. 677,772, Apr. 16, 1976, abandoned.

[51] Int. Cl.$^3$ .................... A61K 31/47; C07D 219/06
[52] U.S. Cl. .......................... 424/257; 544/80; 544/126; 544/361; 546/103; 546/104; 424/248.56; 424/250
[58] Field of Search .............. 546/103, 104; 544/80, 544/126, 361; 424/248, 56, 250, 257

[56] References Cited

U.S. PATENT DOCUMENTS

| | | | |
|---|---|---|---|
| 1,727,480 | 9/1929 | Mietzsch | 546/104 |
| 2,645,594 | 7/1953 | Tabern | 546/102 |
| 2,732,373 | 1/1956 | Steiger | 546/103 |
| 2,732,374 | 1/1956 | Steiger | 546/103 |
| 3,131,190 | 4/1964 | Zirkle | 546/104 |
| 3,131,191 | 4/1964 | Douglas et al. | 546/48 |
| 3,331,849 | 7/1967 | Shavel, Jr. et al. | 546/43 |
| 3,597,430 | 8/1971 | Kaiser et al. | 546/103 |
| 3,615,416 | 10/1971 | Fox | 430/83 |
| 3,740,403 | 6/1973 | Murdock | 546/104 |

FOREIGN PATENT DOCUMENTS 251021 7/1948 Switzerland.

OTHER PUBLICATIONS

Marxer, Helv. Chim. Acta, 49(1), pp. 572–80, (1966), Chemical Abstracts, vol. 64, 12669a.
Albert, "The Acridines," 2nd ed., p. 331, N. Y., St. Martins Press, (1966).

*Primary Examiner*—Jose Tovar
*Assistant Examiner*—Diana G. Rivers
*Attorney, Agent, or Firm*—Thomas L. Johnson; B. Woodrow Wyatt

[57] ABSTRACT

9-Phenyl(or benzyl)acridines, 9-phenyl(or benzyl)-9-acridinols and acridinium compounds, useful as trypanosomacidal and antibacterial agents, are prepared from aminoalkoxy substituted 9-acridinones via reaction with the appropriate Grignard reagents or aryllithium. The intermediate aminoalkoxy substituted 9-acridinones, prepared from the corresponding halo or hydroxy substituted 9-acridinones, are useful as antiviral agents.

10 Claims, No Drawings

ACRIDINE COMPOUNDS AND METHODS OF COMBATTING VIRUSES WITH THEM

This application is a continuation-in-part of application Ser. No. 774,399, filed Mar. 4, 1977, now U.S. Pat. No. 4,150,134, which is in turn a continuation-in-part of application Ser. No. 677,772, filed Apr. 16, 1976, now abandoned.

BACKGROUND OF THE INVENTION

1. Field of the Invention

This invention relates to certain novel acridine compounds, to the preparation thereof, and to compositions and methods for the use thereof in combatting trypanosomal infections.

2. Description of the Prior Art

Dialkylaminoalkoxy substituted 9(10H)-acridinones, unsubstituted on the nitrogen atom stated to be useful as anthelmintic, antifungal and antitrypanosomal agents, are disclosed in Steiger U.S. Pat. Nos. 2,732,373 and 2,732,374 (Jan. 24, 1956).

9-(Alkoxyphenyl)-9-acridinols and 9-(alkoxyphenyl)acridinium salts, stated to be useful as antiseptics, are disclosed in Tabern U.S. Pat. No. 2,645,594 (July 14, 1953).

3,6-Bis(dialkylaminoalkoxy)acridines with hydrogen or alkyl substitution in the 9-position, stated to be useful as remedies against blood parasites, are disclosed in Mietzsch U.S. Pat. No. 1,727,480 (Sept. 10, 1929).

3,6-Bis(dialkylaminoalkoxy)acridines unsubstituted in the 9-position, stated to be useful as antiviral agents, are disclosed in Murdock U.S. Pat. No. 3,740,403 (June 19, 1973).

SUMMARY OF THE INVENTION

In a composition of matter aspect, the invention relates to pharmaceutically acceptable acid-addition salts of compounds of the formula

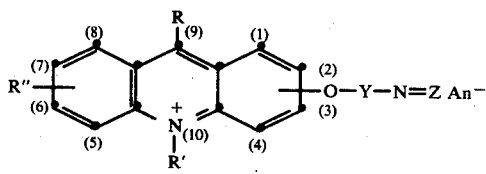

wherein R is phenyl, benzyl, or phenyl or benzyl substituted by a single substituent selected from the group consisting of lower-alkyl, lower-alkoxy or halogen; R' is lower-alkyl or benzyl; R" is hydrogen, chloro or lower-alkoxy; -Y- is lower-alkylene of from two to four carbon atoms wherein the terminal valences are on separate carbon atoms; N=Z is di-lower-alkylamino, piperidino, pyrrolidino, morpholino, or N-methylpiperazino or —Y—N=Z together is 9-methylgranatanin-3-yl; and An— is a pharmaceutically acceptable anion.

In a further composition of matter aspect, the invention relates to compounds of the formula

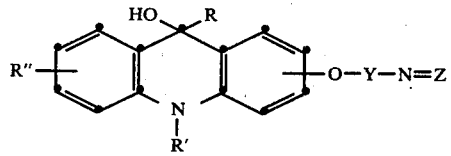

wherein R is phenyl, benzyl, or phenyl or benzyl substituted by a single substituent selected from the group consisting of lower-alkyl, lower-alkoxy or halogen; R' is lower-alkyl or benzyl; R" is hydrogen, chloro or lower-alkoxy; -Y- is lower-alkylene of from two to four carbon atoms wherein the terminal valences are on separate carbon atoms; and N=Z is di-lower-alkylamino, piperidino, pyrrolidino, morpholino, N-methylpiperazino; or —Y—N=Z together is 9-methylgranatanin-3-yl; or a lower-alkyl halide or R°-sulfonate quaternary ammonium salt thereof wherein R° is lower-alkyl or aralkyl.

In a further composition of matter aspect, the invention relates to compounds of the formula

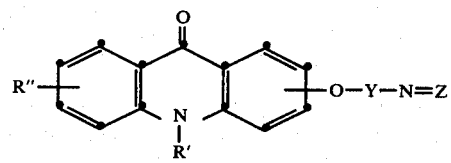

wherein R' is lower-alkyl or benzyl; R" is hydrogen, chloro or lower-alkoxy; —Y— is lower-alkylene of from two to four carbon atoms wherein the terminal valences are on separate carbon atoms; N=Z is piperidino, pyrrolidino, morpholino or N-methylpiperazino; or —Y—N=Z together is 9-methylgranatanin-3-yl; or a pharmaceutically acceptable acid-addition salt thereof.

A particularly preferred species is one according to formula III wherein R' is methyl, R" is hydrogen and —O—Y—N=Z is 1-(2-dimethylaminoethoxy), namely, 1-(2-dimethylaminoethoxy)-10-methyl-9(10H)-acridinone.

The invention further relates to compositions for combatting viruses comprising an antivirally effective amount of at least one compound of formula III in admixture with a suitable carrier or diluent; and to a method for combatting viruses with said compositions.

DETAILED DESCRIPTION INCLUSIVE OF PREFERRED EMBODIMENTS

The 9-acridinones of Formula III are prepared by reacting a compound of the formula

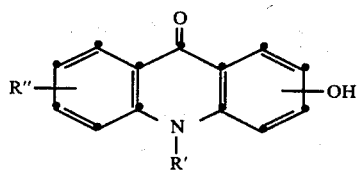

with a compound of the formula Hal—Y—N=Z, wherein Hal is chlorine or bromine in the presence of a strong base; or reacting a compound of the formula

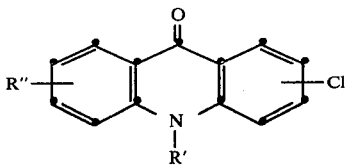

wherein R" is hydrogen or lower-alkoxy with a compound of the formula HO—Y—N=Z in the presence of a strong base.

The compounds of formulas IV and V belong to known classes of compounds, prepared by cyclization of an ortho-arylaminobenzoic acid, followed by N-alkylation. In preparing the compounds of formula IV the hydroxy group is protected in the form of the methyl ether which is finally removed by cleavage with hydrobromic acid.

The preparation of a compound of formula III by reacting a compound of formula IV or V with an amino-alkyl halide (Hal—Y—N=Z) or amino-alkanol (HO—Y—N=Z), respectively, is carried out in the presence of a strong base under essentially anhydrous conditions. The reaction of a compound of formula V with an amino-alkanol (HO—Y—N=Z) is especially useful in preparing compounds of formula III where the basic ether side chain is in the 1- or 3-position of the acridine nucleus.

The 9-acridinols of formula II are prepared by reacting a 9-acridinone of formula III with a compound of the formula RLi or RMg halide. The reaction is carried out in an inert solvent under essentially anhydrous conditions at temperatures ranging from ambient (room) temperature to the reflux temperature of the solvent. The resulting organometallic complex is hydrolyzed with water to give the desired 9-acridinol of formula II.

The 9-acridinols of formula II are readily dehydrated by treatment with a strong acid to give an acridinium salt of formula I where the anion An is that associated with the strong acid used. An acid-addition salt, associated with the terminal amino group of the side chain, is obtained. A preferred method of dehydration comprises treating the acridinol in ethanol containing dissolved hydrogen chloride at a temperature between about 0° C. and the boiling point of the solution (78° C.). This produces an acridinium chloride hydrochloride. Different anions can be obtained by the use of different acids in the dehydration reactions or by conventional ion exchange reactions.

The terms "lower-alkyl" or "lower-alkoxy", wherever used in defining the variables R, R', R" or N=Z, refer to such groups having from one to four carbon atoms which can be straight or branched, preferably primary or secondary alkyl.

The position of the amino-alkoxy side chain can be any of the 1, 2, 3 or 4 positions of the acridine nucleus, the 2 or 3 position being preferred.

The 9-methylgranatanin-3-yl radical, used in the definition of —Y—N=Z, is of the structure:

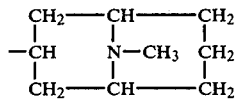

This is an alkylene bridged substituted piperidine and as such can be named as 2,6-trimethylene-1-methyl-4-piperidyl. The systemic name is 9-methyl-9-azabicyclo[3.3.1]non-3-yl.

The exact nature of the anion An or the acid-addition salt anion is not critical provided it is relatively non-toxic to mammals and thus pharmaceutically acceptable. Such acids include the halides, chloride, bromide and iodide; sulfate, nitrate, phosphate, acetate, lactate, tartrate, cyclohexanesulfamate, tosylate, naphthalenesulfonate, and the like.

A quaternary ammonium salt of a compound of formula II is readily formed by interacting a free base of formula II with a lower-alkyl halide, for example, methyl iodide; or a lower-alkyl R°-sulfonate, wherein R° is lower-alkyl or aralkyl, such as methyl p-toluenesulfonate, in an inert organic solvent.

Biological evaluation of the compounds of formulas I and II has shown that they possess trypanosomacidal activity and antimicrobial properties, and are therefore useful in combatting infections caused by trypanosomal organisms such as *Trypanosoma brucei*, and as antiseptic agents. Certain of the compounds have also demonstrated amebicidal and antiviral activity.

The compounds of formula III are not only useful as intermediates in preparing the compounds of formulas I and II but are also useful as antiviral agents.

Trypanosomacidal activity was determined against *Trypanosoma brucei* in mice. In a curative test medication was given (orally or parenterally) as a single dose or daily in equally subdivided doses eight hours apart for four days beginning 72 hours after intraperitoneal infection. In a prophylactic-suppressive test the total daily medication was given as a single treatment one day prior to infection, and thereafter for three consecutive days the total daily medications were administered as equally subdivided doses eight hours apart. The infection was uniformly fatal in five to six days in the absence of therapy. Chemotherapeutic effectiveness was based on extension of survival time. Tests were considered terminated 28 days after infection.

The antimicrobial activity of the compounds was determined in vitro by the conventional serial dilution technique against several species of bacteria and fungi, e.g. *S. aureus, S. pyogenes, C. albicans, T. mentagrophytes.*

Amebicidal activity was determined by oral administration of the test compound orally to hamsters infected with *Endameba criceti* and the amount of drug necessary to clear the animals of infection in three days was determined.

Antiviral activity was determined in vitro by the conventional serial dilution technique against selected virus species such as herpes simplex virus types 1 and 2. In vivo antiviral activity was determined against herpes virus in the mouse genital model and the guinea pig skin infection model.

The compounds can be prepared for use in tablet or capsule form with conventional excipients for oral administration, or in aqueous or oil vehicles for parenteral administration. When used as topical antimicrobial or antiviral agents the compounds can be dissolved in aqueous media and used to disinfect the locus of infection.

The following examples will further illustrate the invention without the latter being limited thereby.

EXAMPLE 1

2-(2-Dimethylaminoethoxy)-10-methyl-9(10H)-acridinone [III; R' is $CH_3$, R" is H, —O—Y—N=Z is 2—O—$CH_2CH_2N(CH_3)_2$]

To a suspension of 45.0 g. (0.2 m.) of 2-hydroxy-10-methyl-9(10H)-acridinone in 680 ml. of chlorobenzene was added 13.7 g. (0.25 m.) of sodium methoxide and 60 ml. of methanol. The mixture was stirred and heated while distilling off the solvent until the pot temperature reached 130° C. The mixture was allowed to cool to 100° C., 38 g. (0.35 m.) of 2-dimethylaminoethyl chloride was added all at once, and the mixture was stirred at reflux for three hours. After the mixture had cooled to 50° C., 250 ml. of water and 50 ml. of 35% aqueous sodium hydroxide were added and the mixture was stirred for 15 minutes. The organic and aqueous layers were separated and the latter extracted with chloroform. The organic solutions were combined, dried over anhydrous magnesium sulfate and the solvent removed to give a yellow solid which was recrystallized from acetonitrile to give 44.1 g. (74%) of 2-(2-dimethylaminoethoxy)-10-methyl-9(10H)-acridinone, m.p. 115°–117° C.

2-(2-Dimethylaminoethoxy)-10-methyl-9(10H)-acridinone was found to be active in vitro against herpes simplex virus type 2 at a concentration of 3–6 micrograms per milliliter.

EXAMPLE 2

(a) 2-Methoxy-10-ethyl-9(10H)-acridinone

To a stirred mixture of 57 g. (0.253 m.) of 2-methoxy-9(10H)-acridinone and 500 ml. of dry dimethylformamide was added in portions 20 g. of 57% sodium hydride in oil (11.4 g., 0.48 m. of NaH). The mixture was stirred for 45 minutes and then 60 ml. (116.4 g., 0.75 m.) of ethyl iodide was added dropwise over a period of 40 minutes. The reaction mixture was stirred for five hours and then poured into water. The resulting solid was collected by filtration, washed with water and recrystallized from ethyl acetate to give 45.1 g. (70%) of 2-methoxy-10-ethyl-9(10H)-acridinone, m.p. 149.5°–152° C.

Similarly, there was prepared, from 3-chloro-9(10H)-acridinone and ethyl acetate, 3-chloro-10-ethyl-9(10H)-acridinone, m.p. 169°–171° C.

(b) 2-Hydroxy-10-ethyl-9(10H)-acridinone [IV; R' is $C_2H_5$, R" is H, OH in 2-position]

A mixture of 37.2 g. (0.147 m.) of 2-methoxy-10-ethyl-9(10H)-acridinone and 350 ml. of 48% aqueous hydrogen bromide was stirred at reflux for six hours. The reaction mixture was diluted with water, and the solid product was collected by filtration, washed with water and recrystallized from ethanol to give 27.0 g. (77%) of 2-hydroxy-10-ethyl-9(10H)-acridinone as a yellow solid, m.p. 241°–246° C. (dec.).

(c) 2-(2-Dimethylaminoethoxy)-10-ethyl-9(10H)-acridinone [III; R' is $C_2H_5$, R" is H, —O—Y—N=Z is 2—O—$CH_2CH_2N(CH_3)_2$]

m.p. 63°–71° C. was prepared in about 50% yield from 2-hydroxy-10-ethyl-9(10H)-acridinone and 2-dimethylaminoethyl chloride according to the method of Example 1. It was also obtained in 78% yield in the form of its hydrochloride salt, m.p. 206°–209° C. (yellow crystals) when recrystallized from an ethanol-ether mixture.

Similarly, employing the appropriate hydroxy-9(10H)-acridinone and aminoalkyl chloride according to Example 1, the following compounds were prepared in yields ranging from 60 to 80 percent.

EXAMPLE 3

2-(3-Dimethylaminopropoxy)-10-methyl-9(10H)-acridinone [III; R' is $CH_3$, R" is H, —O—Y—N=Z is 2—O—$CH_2CH_2CH_2N(CH_3)_2$], m.p. 134°–137° C. (yellow crystals).

EXAMPLE 4

2-(2-Diethylaminoethoxy)-10-methyl-9(10H)-acridinone [III; R' is $CH_3$, R" is H, —O—Y—N=Z is 2—O—$CH_2CH_2N(C_2H_5)_2$], m.p. 97°–100° C.

EXAMPLE 5

2-(2-Dimethylaminoethoxy)-6-chloro-10-methyl-9(10H)-acridinone [III; R' is $CH_3$, R" is Cl, —O—Y—N=Z is 2—O—$CH_2CH_2N(CH_3)_2$], m.p. 197°–201° C.

EXAMPLE 6

2-(2-Diethylaminoethoxy)-6-chloro-10-methyl-9(10H)-acridinone [III; R' is $CH_3$, R" is Cl, —O—Y—N=Z is 2—O—$CH_2CH_2N(C_2H_5)_2$], m.p. 162°–164.5° C.

EXAMPLE 7

2-[2-(1-Pyrrolidyl)ethoxy]-10-methyl-9(10H)-acridinone [III; R' is $CH_3$, R" is H, —O—Y—N=Z is 2—O—$CH_2CH_2N(CH_2)_4$], m.p. 154°–159° C. (yellow crystals); active against herpes simplex virus 1 and 2 at 6 mcg. per ml., and effective in combatting herpes virus 2 genital infection in mice.

EXAMPLE 8

2-[2-(4-Morpholinyl)ethoxy]-10-methyl-9(10H)-acridinone [III; R' is $CH_3$, R" is H, —O—Y—N=Z is 2—O—$CH_2CH_2N(CH_2)_4O$], m.p. 146°–149° C. (yellow needles); active against herpes simplex virus 1 and 2 at 25 mcg. per ml.

EXAMPLE 9

2-[2-(4-Methyl-1-piperazinyl)ethoxy]-10-methyl-9(10H)-acridinone [III; R' is $CH_3$, R" is H, —O—Y—N=Z is 2—O—$CH_2CH_2N(CH_2)_4NCH_3$], m.p. 162°–166° C. (yellow crystals); active against herpes simplex virus 1 and 2 at 25 mcg. per ml.

EXAMPLE 10

2-[2-(1-Piperidyl)ethoxy]-10-methyl-9(10H)-acridinone [III; R' is $CH_3$, R" is H, —O—Y—N=Z is 2—O—$CH_2CH_2N(CH_2)_5$], m.p. 125°–127.5° C. (yellow powder); active against herpes simplex virus 1 at 6 mcg. per ml.

EXAMPLE 11

2-[2-(1-Pyrrolidyl)ethoxy]-10-ethyl-9(10H)-acridinone [III; R' is $C_2H_5$, R" is H, —O—Y—N=Z is 2—O—$CH_2CH_2N(CH_2)_4$], hydrochloride salt, m.p. 216°–220° C. (yellow powder); active against herpes simplex virus 1 and 2 at 25 mcg. per ml.

EXAMPLE 12

4-(2-Dimethylaminoethoxy)-10-methyl-9(10H)-acridinone [III; R' is $CH_3$, R" is H, —O—Y—N=Z is 4—O—$CH_2CH_2N(CH_3)_2$], hydrochloride salt, m.p. 228°–236° C. (tan solid).

EXAMPLE 13

4-[2-(1-Pyrrolidyl)ethoxy]-10-methyl-9(10H)-acridinone [III; R' is CH$_3$, R" is H, —O—Y—N=Z is 4—O—CH$_2$CH$_2$N(CH$_2$)$_4$], hydrochloride salt hemihydrate, m.p. 211°–218° C. (light yellow powder); active against herpes simplex virus 2 at 12 mcg. per ml.

EXAMPLE 14

4-(3-Dimethylaminopropoxy)-10-methyl-9(10H)-acridinone [III; R' is CH$_3$, R" is H, —O—Y—N=Z is 4—O—CH$_2$CH$_2$CH$_2$N(CH$_3$)$_2$], hydrochloride salt, m.p. 204°–209° C. (light yellow powder).

EXAMPLE 15

4-[2-(1-Piperidyl)ethoxy]-10-methyl-9(10H)-acridinone [III; R' is CH$_3$, R" is H, —O—Y—N=Z is 4—O—CH$_2$CH$_2$N(CH$_2$)$_5$], hydrochloride salt, m.p. 251°–256° C. (light yellow powder); active against herpes simplex virus 2 at 12 mcg. per ml.

EXAMPLE 16

2-[4-(1-Pyrrolidyl)butoxy]-10-methyl-9(10H)-acridinone [III; R' is CH$_3$, R" is H, —O—Y—N=Z is 2—O(CH$_2$)$_4$N(CH$_2$)$_4$], m.p. 128°–132° C. (yellow powder); active against herpes simplex virus 1 and 2 at 6 mcg. per ml.

EXAMPLE 17

2-(4-Dimethylaminobutoxy)-10-methyl-9(10H)-acridinone [III; R' is CH$_3$, R" is H, —O—Y—N=Z is 2—O(CH$_2$)$_4$N(CH$_3$)$_2$], dihydrochloride salt, m.p. 215°–231° C. (golden solid).

EXAMPLE 18

2-(2-Diethylaminoethoxy)-10-methyl-9(10H)-acridinone [III; R' is CH$_3$, R" is H, —O—Y—N=Z is 2—O—CH$_2$CH$_2$N(C$_2$H$_5$)$_2$], hydrochloride salt, m.p. 225°–231° C. (yellow powder).

EXAMPLE 19

3-(2-Dimethylaminoethoxy)-10-methyl-9(10H)-acridinone [III; R' is CH$_3$, R" is H, —O—Y—N=Z is 3—O—CH$_2$CH$_2$N(CH$_3$)$_2$]

A mixture of 48.8 g. (0.2 m.) of 3-chloro-10-methyl-9(10H)-acridinone and 500 ml. of dry dimethylformamide was stirred and heated to 65° C. There was then added all at once 71 g. (0.8 m.) of 2-dimethylaminoethanol, followed by 44.8 g. (0.4 m.) of potassium tertiary-butoxide in portions over a 30 minute period. The reaction mixture was stirred at 60°–65° C. for five hours and then poured into cold water. The solid product was collected, washed with water and recrystallized from acetonitrile to give 54.5 g. (92%) of 3-(2-dimethylaminoethoxy)-10-methyl-9(10H)-acridinone, m.p. 152°–155° C.

Similarly, employing the appropriate chloro-9(10H)-acridinone and amino-alkanol, the following compounds were prepared in 60–80% yield:

EXAMPLE 20

3-(3-Dimethylaminopropoxy)-10-methyl-9(10H)-acridinone [III; R' is CH$_3$, R" is H, —O—Y—N=Z is 3—O—CH$_2$CH$_2$CH$_2$N(CH$_3$)$_2$], double m.p. 116.5°–119.5° C.; 127°–129° C., pale green crystals.

EXAMPLE 21

3-[2-(1-Pyrrolidyl)ethoxy]-10-methyl-9(10H)-acridinone [III; R' is CH$_3$, R" is H, —O—Y—N=Z is 3-O-CH$_2$CH$_2$N(CH$_2$)$_4$], m.p. 117°–120° C., light yellow crystals.

EXAMPLE 22

3-(2-Diethylaminoethoxy)-10-methyl-9(10H)-acridinone [III; R' is CH$_3$, R" is H, —O—Y—N=Z is 3-O-CH$_2$CH$_2$N(C$_2$H$_5$)$_2$], m.p. 92.5°–95° C.

EXAMPLE 23

3-(2-Dimethylaminoethoxy)-10-ethyl-9(10H)-acridinone [III; R' is C$_2$H$_5$, R" is H, —O—Y—N=Z is 3-O-CH$_2$CH$_2$N(CH$_3$)$_2$], m.p. 114.5°–117° C.

EXAMPLE 24

3-(2-Dimethylaminoethoxy)-7-methoxy-10-methyl-9(10H)-acridinone [III; R' is CH$_3$, R" is 7-CH$_3$O, —O—Y—N=Z is 3-O-CH$_2$CH$_2$N(CH$_3$)$_2$], m.p. 139°–145° C. (yellow plates).

EXAMPLE 25

3-(2-Diethylaminoethoxy)-7-methoxy-10-methyl-9(10H)-acridinone [III; R' is CH$_3$, R" is 7-CH$_3$O, —O—Y—N=Z is 3-O-CH$_2$CH$_2$N(C$_2$H$_5$)$_2$], m.p. 108°–110° C. (pale yellow solid).

EXAMPLE 26

3-(2-Dimethylaminoethoxy)-10-benzyl-9(10H)-acridinone [III; R' is C$_6$H$_5$CH$_2$, R" is H, —O—Y—N=Z is 3-O-CH$_2$CH$_2$N(CH$_3$)$_2$], m.p. 134°–136° C. (light yellow powder). The intermediate 3-chloro-10-benzyl-9(10H)-acridinone, m.p. 186°–190° C. (yellow crystals) was prepared from 3-chloro-9(10H)-acridinone and benzyl bromide with sodium hydride in dimethylformamide.

EXAMPLE 27

1-(2-Dimethylaminoethoxy)-10-methyl-9(10H)-acridinone [III; R' is CH$_3$, R" is H, —O—Y—N=Z is 1-O-CH$_2$CH$_2$N(CH$_3$)$_2$], hydrochloride salt, m.p. 237°–241° C. (tan granules from methanol-ether). The intermediate 1-chloro-10-methyl-9(10H)-acridinone, m.p. 183°–186° C. (pale yellow granules from ethanol) was prepared by N-methylation of 1-chloro-9(10H)-acridinone, in turn prepared by cyclization of 2-(m-chlorophenylamino)benzoic acid with sulfuric acid.

1-(2-Dimethylaminoethoxy)-10-methyl-9(10H)-acridinone hydrochloride was active in vitro against herpes simplex virus types 1 and 2 at 6 mcg. per ml.; and at 4–10 mg./ml. it reduced the plaque counts of six herpes simplex strains by at least 50%. In in vivo studies the compound afforded 50–90% survival in mice with genital herpes simplex type 2 infection at concentrations ranging from 2.5 to 10%; and reduced the virus titer of herpes simplex virus type 1 in guinea pig skin infection by more than 99% after 48 hours of topical treatment. Also, 100–200 mg/kg/day of the compound caused a significant reduction in influenza virus A$_2$/Jap 170 titers in ferret nasal washings.

EXAMPLE 28

1-(2-Diethylaminoethoxy)-10-methyl-9(10H)-acridinone [III; R' is CH$_3$, R" is H, —O—Y—N=Z is 1-O-CH$_2$CH$_2$N(C$_2$H$_5$)$_2$], hydrochloride salt, m.p. 226°–232° C., pale yellow powder.

EXAMPLE 29

1-[2-(1-Pyrrolidinyl)ethoxy]-10-methyl-9(10H)-acridinone [III; R' is CH$_3$, R" is H, —O—Y—N=Z is 1-O-CH$_2$CH$_2$N(CH$_2$)$_4$], hydrochloride salt, m.p. 221°–225° C. (light yellow powder from ethanol-ether).

EXAMPLE 30

3-[2-(4-Morpholinyl)ethoxy]-10-methyl-9(10H)-acridinone [III; R' is CH$_3$, R" is H, —O—Y—N=Z is 3-O-CH$_2$CH$_2$N(CH$_2$)$_4$O], m.p. 140°–143° C. (tan crystals).

EXAMPLE 31 exo-3-(9-Methylgranatanin-3-yloxy)-10-methyl-9(10H)-acridinone [III; R' is CH$_3$, R" is H, —O—Y—N=Z is 3-(9-methylgranatanin-3-yloxy)], m.p. 155°–157° C. (tan powder).

EXAMPLE 32

1-(3-Dimethylaminopropoxy)-10-methyl-9(10H)-acridinone [III; R' is CH$_3$, R" is H, —O—Y—N=Z is 1-O(CH$_2$)$_3$N(CH$_3$)$_2$], hydrochloride salt, m.p. 211°–215° C. (yellow granules).

EXAMPLE 33

1-[2-(1-Piperidyl)ethoxy]-10-methyl-9(10H)-acridinone [III; R' is CH$_3$, R" is H, —O—Y—N=Z is 1-O(CH$_2$)$_2$N(CH$_2$)$_5$], m.p. 112°–114° C. (yellow crystals); active against herpes simplex virus 1 at 6 mcg. per ml.

EXAMPLE 34 exo-1-(9-Methylgranatanin-3-yloxy)-10-methyl-9(10H)-acridinone [III; R' is CH$_3$, R" is H, —O—Y—N=Z is 1-(9-methylgranatanin-3-yloxy)], m.p. 106°–132° C. (yellow powder); active against herpes simplex virus 1 and 2 at 25 mcg. per ml.

EXAMPLE 35

4-(Diethylaminoethoxy)-10-methyl-9(10H)-acridinone [III; R' is CH$_3$, R" is H, —O—Y—N=Z is 4-O-CH$_2$CH$_2$N(C$_2$H$_5$)$_2$], hydrochloride salt, m.p. 203°–207° C. (yellow powder).

EXAMPLE 36

2-(2-Dimethylaminoethoxy)-9,10-dihydro-10-methyl-9-phenyl-9-acridinol [II; R is C$_6$H$_5$, R' is CH$_3$, R" is H, —O—Y—N=Z is 2-O-CH$_2$CH$_2$N(CH$_3$)$_2$]

To a solution of 17.8 g. (0.06 m.) of 2-(2-dimethylaminoethoxy)-10-methyl-9(10H)-acridinone (Example 1) in 300 ml. of dry benzene at about 35° C. was added, dropwise, 40 ml. (0.08 m.) of 2 M phenyllithium in benzene-ether solution. The reaction mixture was stirred for three hours and allowed to stand overnight. Water (20 ml.) was then added dropwise and the mixture was dried over anhydrous magnesium sulfate. The solvent was removed in vacuo at 45° C. and the residue crystallized from acetonitrile to give 11.2 g. (50%) of 2-(2-dimethylaminoethoxy)-9,10-dihydro-10-methyl-9-phenyl-9-acridinol. A second recrystallization from acetonitrile gave a sample with m.p. 157°–161° C. (dec.).

EXAMPLE 37

2-(2-Dimethylaminoethoxy)-9,10-dihydro-10-methyl-9-phenyl-9-acridinol

To a solution of 270 g. (0.8 m.) of 2-(2-dimethylaminoethoxy)-10-methyl-9(10H)-acridinone (Example 1) in 4 liters of dimethylformamide was added 450 ml. of phenylmagnesium bromide (2.9 molar in ether, 1.45 m.) over a one hour period. The reaction mixture was stirred for one hour longer and then added to 22 liters of cold water. The solid product was collected by filtration, slurried with 2 liters of chloroform and filtered. The chloroform filtrate was washed with water, decolorized with activated charcoal and concentrated in vacuo at below 25° C. to a volume of 300 ml. whereupon the solid product separated. The latter was collected, washed with chloroform and n-hexane and dried in vacuo at 25° C. overnight and two hours at 35° C. to give 186 g. (62%) of 2-(2-dimethylaminoethoxy)-9,10-dihydro-10-methyl-9-phenyl-9-acridinol in the form of a monohydrate, m.p. 162°–164° C. (dec.). An additional 21 g. (7%), m.p. 156°–159° C. was obtained from the mother liquors.

2-(2-Dimethylaminoethoxy)-9,10-dihydro-10-methyl-9-phenyl-9-acridinol (15.7 g.) and 25 g. of methyl p-toluenesulfonate in 500 ml. of tetrahydrofuran were held at room temperature for six hours. The mixture was cooled, and the solid product was collected and recrystallized from acetonitrile to give 16.1 g. (71%) of the methyl p-toluenesulfonate quaternary ammonium salt of 2-(2-dimethylaminoethoxy)-9,10-dihydro-10-methyl-9-phenyl-9-acridinol, beige powder, m.p. 109°–114° C.

2-(2-Dimethylaminoethoxy)-9,10-dihydro-10-methyl-9-phenyl-9-acridinol was completely effective orally in the curative test against a murine infection with *Trypanosoma brucei* at a dose level of 25 mg per kg per day for four days; and was completely effective orally in the prophylactic test at a dose level of 50 mg per kg per day. The compound was also completely effective when administered intraperitoneally, subcutaneously or intramuscularly as a single dose of 200 mg/kg three days after infection of the mice.

In a manner similar to the procedure of Example 36 above, employing the appropriate aminoethoxy-10-alkyl-9(10H)-acridinone and phenyllithium, there was obtained the following compounds in 40–85% yield:

EXAMPLE 38

2-(2-Diethylaminoethoxy)-9,10-dihydro-10-methyl-9-phenyl-9-acridinol [II; R is C$_6$H$_5$, R' is CH$_3$, R" is H, —O—Y—N=Z is 2-O-CH$_2$CH$_2$N(C$_2$H$_5$)$_2$], mottled-purple powder, m.p. 110°–112.5° C. This compound was completely effective orally in the curative test against a murine infection with *T. brucei* at a dose level of 50 mg/kg/day×4.

EXAMPLE 39

3-(3-Dimethylaminopropoxy)-9,10-dihydro-10-methyl-9-phenyl-9-acridinol [II; R is C$_6$H$_5$, R' is CH$_3$, R" is H, —O—Y—N=Z is 3-O-CH$_2$CH$_2$CH$_2$N(CH$_3$)$_2$], pale lavender crystals, m.p. 142°–148° C. (dec.).

EXAMPLE 40

3-(2-Dimethylaminoethoxy)-9,10-dihydro-10-methyl-9-phenyl-9-acridinol [II; R is C$_6$H$_5$, R' is CH$_3$, R" is H, —O—Y—N=Z is 3-O-CH$_2$CH$_2$N(CH$_3$)$_2$], pale rose crystals, m.p. 132°–136° C. (dec.).

EXAMPLE 41

3-[2-(1-Pyrrolidyl)ethoxy]-9,10-dihydro-10-methyl-9-phenyl-9-acridinol [II; R is C$_6$H$_5$, R' is CH$_3$, R" is H, —O—Y—N=Z is 3-O-CH$_2$CH$_2$N(CH$_2$)$_4$], m.p. 154°–158° C., salmon colored crystals.

EXAMPLE 42

3-(2-Diethylaminoethoxy)-9,10-dihydro-10-methyl-9-phenyl-9-acridinol [II; R is $C_6H_5$, R' is $CH_3$, R" is H, —O—Y—N=Z is 3-O-$CH_2CH_2N(C_2H_5)_2$], m.p. 145°–148° C., pale orange crystals.

EXAMPLE 43

2-(2-Dimethylaminoethoxy)-6-chloro-9,10-dihydro-10-methyl-9-phenyl-9-acridinol [II; R is $C_6H_5$, R' is $CH_3$, R" is Cl, —O—Y—N=Z is 2-O-$CH_2CH_2N(CH_3)_2$], m.p. 161°–164° C., rose crystals.

EXAMPLE 44

2-(2-Diethylaminoethoxy)-6-chloro-9,10-dihydro-10-methyl-9-phenyl-9-acridinol [II; R is $C_6H_5$, R' is $CH_3$, R" is Cl, —O—Y—N=Z is 2-O-$CH_2CH_2N(C_2H_5)_2$], m.p. 105°–108° C., pale pink powder.

EXAMPLE 45

3-(2-Dimethylaminoethoxy)-10-benzyl-9-phenyl-9-acridinol [II; R is $C_6H_5$, R' is $CH_2C_6H_5$, R" is H, —O—Y—N=Z is 3-O-$CH_2CH_2N(CH_3)_2$], m.p. 97°–103° C., light pink powder.

EXAMPLE 46

3-(2-Dimethylaminoethoxy)-10-ethyl-9,10-dihydro-9-phenyl-9-acridinol [II; R is $C_6H_5$, R' is $C_2H_5$, R" is H, —O—Y—N=Z is 3-O-$CH_2CH_2N(CH_3)_2$], m.p. 166°–170° C. (dec.), salmon needles.

EXAMPLE 47

3-[2-(4-Morpholinyl)ethoxy]-10-methyl-9,10-dihydro-9-phenyl-9-acridinol [II; R is $C_6H_5$, R' is $CH_3$, R" is H, —O—Y—N=Z is 3-O-$CH_2CH_2N(CH_2)_4O$], m.p. 158°–161° C. (dec.), white needles.

EXAMPLE 48

2-[2-(1-Pyrrolidyl)ethoxy]-10-methyl-9,10-dihydro-9-phenyl-9-acridinol [II; R is $C_6H_5$, R' is $CH_3$, R" is H, —O—Y—N=Z is 2-O-$CH_2CH_2N(CH_2)_4$], m.p. 145°–148° C., pale green crystals.

EXAMPLE 49

2-(3-Dimethylaminopropoxy)-10-methyl-9,10-dihydro-9-phenyl-9-acridinol [II; R is $C_6H_5$, R' is $CH_3$, R" is H, —O—Y—N=Z is 2-O-$CH_2CH_2CH_2N(CH_3)_2$], m.p. 155°–159° C., off-white solid.

EXAMPLE 50

2-[2-(4-Morpholinyl)ethoxy]-10-methyl-9,10-dihydro-9-phenyl-9-acridinol [II; R is $C_6H_5$, R' is $CH_3$, R" is H, —O—Y—N=Z is 2-O-$CH_2CH_2N(CH_2)_4O$], m.p. 150°–155° C. (dec.), grey solid.

EXAMPLE 51

2-(3-Diethylaminopropoxy)-10-methyl-9,10-dihydro-9-phenyl-9-acridinol [II; R is $C_6H_5$, R' is $CH_3$, R" is H, —O—Y—N=Z is 2-O-$CH_2CH_2CH_2N(C_2H_5)_2$], m.p. 114°–118° C. (dec.), tan crystals.

EXAMPLE 52

2-(2-Dimethylaminoethoxy)-10-ethyl-9,10-dihydro-9-phenyl-9-acridinol [II; R is $C_6H_5$, R' is $C_2H_5$, R" is H, —O—Y—N=Z is 2-O-$CH_2CH_2N(CH_3)_2$], m.p. 156°–161° C. (dec.), pale green powder.

EXAMPLE 53

2-[2-(1-Piperidyl)ethoxy]-10-methyl-9,10-dihydro-9-phenyl-9-acridinol [II; R is $C_6H_5$, R' is $CH_3$, R" is H, —O—Y—N=Z is 2-O-$CH_2CH_2N(CH_2)_5$], m.p. 145°–149° C. (dec.), off-white granules.

EXAMPLE 54

1-(2-Dimethylaminoethoxy)-10-methyl-9,10-dihydro-9-phenyl-9-acridinol [II; R is $C_6H_5$, R' is $CH_3$, R" is H, —O—Y—N=Z is 1-O-$CH_2CH_2N(CH_3)_2$], m.p. 168°–173° C. (dec.), pale green crystals.

EXAMPLE 55

2-[2-(4-Methyl-1-piperazinyl)ethoxy]-10-methyl-9,10-dihydro-9-phenyl-9-acridinol [II; R is $C_6H_5$, R' is $CH_3$, R" is H, —O—Y—N=Z is 2-O-$CH_2CH_2N(CH_2)_4NCH_3$], not purified but converted directly to acridinium compound of Example 73 below.

EXAMPLE 56

4-(2-Dimethylaminoethoxy)-10-methyl-9,10-dihydro-9-phenyl-9-acridinol [II; R is $C_6H_5$, R' is $CH_3$, R" is H, —O—Y—N=Z is 4-O-$CH_2CH_2N(CH_3)_2$], m.p. 147°–151° C., light violet solid.

EXAMPLE 57

1-(2-Diethylaminoethoxy)-9,10-dihydro-10-methyl-9-phenyl-9-acridinol [II; R is $C_6H_5$, R' is $CH_3$, R" is H, —O—Y—N=Z is 1-O-$CH_2CH_2N(C_2H_5)_2$], m.p. 138°–141° C., pale green crystals.

EXAMPLE 58

1-[2-(1-Pyrrolidyl)ethoxy]-9,10-dihydro-10-methyl-9-phenyl-9-acridinol [II; R is $C_6H_5$, R' is $CH_3$, R" is H, —O—Y—N=Z is 1-O-$CH_2CH_2N(CH_2)_4$], m.p. 155°–161° C. (dec.), greenish crystals.

EXAMPLE 59

1-(3-Dimethylaminopropoxy)-9,10-dihydro-10-methyl-9-phenyl-9-acridinol [II; R is $C_6H_5$, R' is $CH_3$, R" is H, —O—Y—N=Z is 1-O$(CH_2)_3N(C_3)_2$], m.p. 102°–104° C., pale green crystals.

EXAMPLE 60

4-[2-(1-Pyrrolidyl)ethoxy]-9,10-dihydro-10-methyl-9-phenyl-9-acridinol [II; R is $C_6H_5$, R' is $CH_3$, R" is H, —O—Y—N=Z is 4-O-$CH_2CH_2N(CH_2)_4$], m.p. 149°–152° C., off-white crystals.

EXAMPLE 61

4-(3-Dimethylaminopropoxy)-9,10-dihydro-10-methyl-9-phenyl-9-acridinol [II; R is $C_6H_5$, R' is $CH_3$, R" is H, —O—Y—N=Z is 4-O$(CH_2)_3N(CH_3)_2$], m.p. 143°–149° C., tan crystals.

EXAMPLE 62

2-(4-Dimethylaminobutoxy)-9,10-dihydro-10-methyl-9-phenyl-9-acridinol [II; R is $C_6H_5$, R;40 is $CH_3$, R" is H, —O—Y—N=Z is 2-O$(CH_2)_4N(CH_3)_2$], m.p. 156°–160° C. (dec.), off-white powder.

EXAMPLE 63 exo-3-(9-Methylgranatanin-3-yloxy)-9,10-dihydro-10-methyl-9-phenyl-9-acridinol [II; R is $C_6H_5$, R' is $CHHd_3$, R" is H, —O—Y—N=Z is 3-(9-methylgranatanin-3-yloxy)], m.p. 159°–165° C. (dec.) rose crystals; active at 3.13 mcg. in vitro vs. Staph. aureus.

EXAMPLE 64 exo-1-(9-Methylgranatanin-3-yloxy)-9,10-dihydro-10-methyl-9-phenyl-9-acridinol [II; R is $C_6H_5$, R' is $CH_3$, R" is H, —O—Y—N=Z is 1-(9-methylgranatanin-3-yloxy)], m.p. 187°–194° C. (dec.) blue crystals.

EXAMPLE 65

2-(2-Dimethylaminoethoxy)-9,10-dihydro-9-(4-methoxyphenyl)-10-methyl-9-acridinol [II; R is 4—$CH_3OC_6H_4$, R" is H, —O—Y—N'Z is 2—O—$CH_2CH_2N(CH_3)_2$]

4-Methoxyphenylmagnesium bromide 8;b 33 ml. of 1.4 M in tetrahydrofuran, 0.04 m). was added, dropwise, to a solution of 11.84 g (0.4 m.) of 2-(2-dimethylaminoethoxy)-10-methyl-9(10H)-acridinone (Example 1) in 200 ml. of benzene. The reaction mixture was stirred for 5.5 hours at room temperature and allowed to stand overnight. Water (15 ml.) was then added, the mixture filtered and the filtrate dried over anhydrous magnesium sulfate. The solvent was removed in vacuo at 50° C. and the residue crystallized from acetonitrile to give 6.4 g. (40%) of 2-(2-dimethylaminoethoxy)-9,10-dihydro-9-(4-methoxyphenyl)-10-methyl-9-acridinol. A sample when recrystallized from acetonitrile had the m.p. 144°–149° C. (dec.) (pale pink powder).

2-(2-Dimethylaminoethoxy)-9,10-dihydro-9-(4-methoxyphenyl)-10-methyl-9-acridinol was completely effective orally in the curative test against a murine infection with *T. brucei* at a dose level of 200 mg/kg/day×4.

In a manner similar to the procedure of Example 65, employing the appropriate aminoethoxy-10-alkyl-9(10H)-acridinone and R-Mg-halide, there were obtained the following compounds:

EXAMPLE 66

4-(2-Dimethylaminoethoxy)-9,10-dihydro-10-methyl-9-benzyl-9-acridinol [II; R is $C_6H_5CH_2$, R' is $CH_3$, R" is H, —O—Y—N=Z is 4—O—$_2CH_2N(CH_3)_2$], m.p. 126°–135° C., yellow granules.

EXAMPLE 67

2-(2-Dimethylaminoethoxy)-9,10-dihydro-10-methyl-9-(2-methyl-phenyl)-9acridinol [II; R is 2-$CH_3C_6H_4$, R' is $CH_3$, R" is H, —O—Y—N=Z is 2-O-$CH_2CH_2N(CH_3)_2$], m.p. 132°–137° C., maroon crystals.

EXAMPLE 68

2-(2-Dimethylaminoethoxy)-10-methyl-9-phenylacridinium chloride hydrochloride [I; R is $C_6H_5$, R' is $CH_3$, R" is H, —O—Y—N=Z is 2-O-$CH_2CH_2N(CH_3)_2$, An is Cl]

To a solution prepared from 2.62 g. (0.007 m.) of 2-(2-dimethylaminoethoxy)-9,10-dihydro-10-methyl-9-phenyl-9-acridinol (Example 36) and 125 ml. of boiling absolute ethanol was added 3 ml. (0.02 m.) of 7 N ethanolic hydrogen chloride. The solution was then diluted with 325 ml. of absolute ether and cooled. The solid product which separated was collected, washed with acetone and dried at 90° C. to give 2.7 g. (86%) of 2-(2-dimethylaminoethoxy)-10-methyl-9-phenylacridinium chloride hydrochloride in the from of a monohydrate, orange needles, m.p. 194°–197° C. (dec.).

In another run 120 g. of the 9-acridinol was slurried in 1050 ml. of absolute ethanol and 60 ml. of concentrated aqueous hydrochloric acid was added over a two minute period. The mixture was stirred for 85 minutes and the product isolated by diluting the solution with ether while seeding with a sample of the desired product. There was obtained 91 g. (61%) of 2-(2-dimethylaminoethoxy)-10-methyl-9-phenylacridinium chloride hydrochloride in the form of a monohydrate, m.p. 215°–218° C.

2-(2-Dimethylaminoethoxy)-10-methyl-9-phenylacridinium chloride was completely effective orally in the curative test against a murine infection with *T. brucei* at a dose level of 25 mg/kg/day×4. The compound was toxic upon parenteral administration but showed some curative effect at the 50 mg/kg dose level.

EXAMPLE 69

2-(2-Dimethylaminoethoxy)-10-methyl-9-phenylacridinium chloride hydrochloride

A solution containing 0.23 mole of phenylmagnesium bromide was prepared by diluting 78 ml. of 3.0 M phenylmagnesium bromide in ether with 200 ml. of dry tetrahydrofuran. This solution was added to a thin slurry of 46.0 g. (0.155 m.) of 2-(2-dimethylaminoethoxy)-10-methyl-9(10H)-acridinone (Example 1) in 460 ml. of tetrahydrofuran over a 2.5 hr. period. The internal temperature stayed below 32° C. during this addition. After 16 hrs. of stirring, 15 ml. of water was cautiously added to the reaction mixture and the solvent was removed under reduced pressure. The mushy residue was slurried with 300 ml. of chloroform and filtered. The filtrate was washed once with 200 ml. of water, dried over sodium sulfate and the chloroform was removed in vacuo to leave 66 g. of dark residue. This residue was slurried in 165 ml. of ethanol, treated with 33.4 ml. (0.4 m.) of concentrated hydrochloric acid and then stirred for 30 min. at room temperature. The dark solution was diluted with 250 ml. of ether and then it was stirred as a heavy yellow precipitate formed. After chilling in an ice bath, the product was collected and dried overnight in vacuo at 60° C. to give 52.0 g. (75%), 2-(2-dimethylaminoethoxy)-10-methyl-9-phenylacridinium chloride hydrochloride in the form of a monohydrate, m.p. 200°–202° C., identical with the compound obtained in Example 68.

By procedure similar to that used in Example 68, employing the appropriate 9-acridinol compound, the following compounds were prepared:

EXAMPLE 70

3-(3-Dimethylaminopropoxy)-10-methyl-9-(4-methoxyphenyl)acridinium chloride hydrochloride [I; R is 4-$CH_3OC_6H_4$, R' is $CH_3$, R" is H, —O;13 Y—N=Z is 3-O-$CH_2CH_2CH_2N(CH_3)_2$, An is Cl], monohydrate, orange powder, m.p. 162°–168° C. (dec.).

EXAMPLE 71

3-(2-Dimethylaminoethoxy)-10-methyl-9-phenylacridinium chloride hydrochloride [I; R is $C_6H_5$, R' is $CH_3$, R" is H, —O—Y—N=Z is 3-O-$CH_2CH_2N(CH_3)_2$, An is Cl], monohydrate, m.p. 157°–163° C. (dec.).

EXAMPLE 72

2-[2-(4-Morpholinyl)ethoxy]-10-methyl-9-phenylacridinium chloride hydrochloride [I; R is $C_6H_5$, R' is $CH_3$, R" is H, —O—Y—N=Z is 2-O-$CH_2CH_2N(CH_2)_4O$, An is Cl], hemihydrate ethanolate, m.p. 172°–177° C. (dec.) (yellow granules from ethanol-ether).

EXAMPLE 73

2-[2-(1-Pyrrolidyl)ethoxy]-10-methyl-9-phenylacridinium chloride hydrochloride [I; R is $C_6H_5$, R' is $CH_3$, R'' is H, —O—Y—N=Z is 2-O-$CH_2CH_2N(CH_2)_4$, An is Cl], monohydrate, m.p. 192°–194° C. (dec.) (yellow plates).

EXAMPLE 74

2-[2-(4-Methyl-1-piperazinyl)ethoxy]-10-methyl-9-phenylacridinium chloride dihydrochloride [I; R is $C_6H_5$, R' is $CH_3$, R'' is H, —O—Y—N=Z is 2-O-$CH_2CH_2N(CH_2)_4NCH_3$, An is Cl], monohydrate, m.p. 215°–225° C. (dec.), orange powder.

EXAMPLE 75

2-[2-(1-Piperidyl)ethoxy]-10-methyl-9-phenylacridinium chloride hydrochloride [I; R is $C_6H_5$, R' is $CH_3$, R'' is H, —O—Y—N=Z is 2-O-$CH_2CH_2N(CH_2)_5$, An is Cl], hydrate, m.p. 198°–201° C. (dec.), yellow crystals.

EXAMPLE 76

1-(2-Dimethylaminoethoxy)-10-methyl-9-phenylacridinium chloride trihydrochloride [I; R is $C_6H_5$, R' is $CH_3$, R'' is H, —O—Y—N=Z is 1-O-$CH_2CH_2N(CH_3)_2$, An is Cl], m.p. 222°–225° C., reddish-orange crystals.

EXAMPLE 77

4-(3-Dimethylaminopropoxy)-10-methyl-9-phenylacridinium chloride hydrochloride [I; R is $C_6H_5$, R' is $CH_3$, R'' is H, —O—Y—N=Z is 4-O-$CH_2CH_2CH_2N(CH_3)_2$], hydrate, m.p. 108°–112° C. (dec.), reddish-orange powder.

According to the procedure described above in Example 65, it is contemplated that each of 2-(2-dimethylaminoethoxy)-9,10-dihydro-10-ethyl-9-phenyl-9-acridinol and 4-(2-dimethylaminoethoxy)-9,10-dihydro-10-methyl-9-phenyl-9-acridinol can be dehydrated with hydrochloric acid to produce the hydrochloride of 2-(2-dimethylaminoethoxy)-10-ethyl-9-phenylacridinium chloride and 4-(2-dimethylaminoethoxy)-10-methyl-9-phenylacridinium chloride, respectively.

EXAMPLE 78

2-(2-Dimethylaminoethoxy)-10-methyl-9-benzylacridinium chloride hydrochloride [I; R is $CH_2C_6H_5$, R' is $CH_3$, R'' is H, —O—Y—N=Z is 2-O-$CH_2CH_2N(CH_3)_2$, An is Cl]

To the Grignard reagent prepared from magnesium and 19.2 g. (0.151 m.) of benzyl chloride in 200 ml. of absolute ether was added, dropwise with stirring, 14.24 g. (0.048 m.) of 2-(2-dimethylaminoethoxy)-10-methyl-9(10H)-acridinone (Example 1) in 300 ml. of benzene. The reaction mixture was heated at reflux for ten hours. Water was then added dropwise until the organometallic complex was hydrolyzed, and the mixture was filtered. The filtrate was dried over anhydrous magnesium sulfate and the solvent removed in vacuo. The residue comprising 2-(2-dimethylaminoethoxy)-9,10-dihydro-10-methyl-9-benzyl-9-acridinol [II; R is $CH_2C_6H_5$, R' is $CH_3$, R'' is H, —O—Y—N=Z is 2-O-$CH_2CH_2N(CH_3)_2$] was warmed with excess ethanolic hydrogen chloride. The solid which formed upon cooling the mixture was collected and recrystallized from an ethanol-ether mixture to give 11.9 g. of 2-(2-dimethylaminoethoxy)-10-methyl-9-benzylacridinium chloride hydrochloride in the form of a dihydrate. A sample when recrystallized from ethanol-ether had the m.p. 216°–218° C. (orange needles).

2-(2-Dimethylaminoethoxy)-10-methyl-9-benzylacridinium chloride was completely effective orally in the curative test against a murine infection with *T. brucei* at a dose level of 100 mg/kg/day×4. It was also active orally against *Endameba criceti* in hamsters at 100 mg/kg.

By procedures similar to that used in Example 78, employing the appropriate 9-acridinone compound, and proceeding through the intermediate 9-benzyl-9-acridinol compound without isolation thereof, the following compounds were prepared:

EXAMPLE 79

2-(2-Dimethylaminoethoxy)-10-methyl-9-(4-fluorobenzyl)acridinium chloride hydrochloride [I; R is $CH_2C_6H_4F-4$, R' is $CH_3$, R'' is H, —O—Y—N=Z is 2-O-$CH_2CH_2N(CH_3)_2$, An is Cl], hydrate (1.5 $H_2O$), orange needles, m.p. 182°–185° C. This compound was completely effective orally in the curative test against a murine infection with *T. brucei* at a dose level of 200 mg/kg/day×4. It was also active orally against *Endameba criceti* in hamsters at 100 l mg/kg.

EXAMPLE 80

2-(2-Dimethylaminoethoxy)-10-methyl-9-(4-methylbenzyl)acridinium chloride hydrochloride [I; R is $CH_2C_6H_4CH_3$, R' is $CH_3$, R'' is H, —O—Y—N=Z is 2-O-$CH_2CH_2N(CH_3)_2$, An is Cl], hydrate (1.5 $H_2O$), yellow powder, m.p. 170°–178° C. (dec.). This compound was ineffective orally in the curative test against a murine infection with *T. brucei* at a dose level of 200 mg/kg/day×4, but showed bacteriostatic activity against *S. aureus* and *S. pyrogenes*, minimum inhibitory concentration (MIC) 15.6 µg/ml and 7.8 µg/ml, respectively.

EXAMPLE 81

3-(2-Dimethylaminoethoxy)-10-methyl-9-benzylacridinium chloride hydrochloride [I; R is $CH_2C_6H_5$, R' is $CH_3$, R'' is H, —O—Y—N=Z is 3-O-$CH_2CH_2N(CH_3)_2$, An is Cl], dihydrate, orange powder, m.p. 170°–178° C.(dec.). This compound was completely effective orally in the curative test against a murine infection with *T. brucei* at a dose level of 100 mg/kg/day×4; and showed bacteriostatic activity against *S. aureus* and *S. pyrogenes* at MIC 31.3 µg/ml.

EXAMPLE 82

3-(3-Dimethylaminopropoxy)-10-methyl-9-benzylacridinium chloride hydrochloride [I; R is $CH_2C_6H_5$, R' is $CH_3$, R'' is H, —O—Y—N=Z is 3-O-$CH_2CH_2CH_2N(CH_3)_2$, An is Cl], dihydrate, orange powder, m.p. 168°–173° C.(dec.). This compound was completely effective orally in the curative test against a murine infection with *T. brucei* at a dose level of 100 mg/kg/day×4; and showed bacteriostatic activity against *S. aureus* at MIC 31.3 µg/ml.

EXAMPLE 83

2-(2-Dimethylaminoethoxy)-10-methyl-9-(4-chlorobenzyl)acridinium chloride hydrochloride [I; R is $CH_2C_6H_4Cl-4$, R' is $CH_3$, R'' is H, —O—Y—N=Z is 2-O-$CH_2CH_2N(CH_3)_2$, An is Cl], hydrate (1.5 $H_2O$), orange solid, m.p. 170°–175° C.(dec.). This compound was ineffective orally in the curative test against a murine infection with *T. brucei* at a dose level of 200 mg/kg/day×4, but showed bacteriostatic activity against *S. aureus* at MIC 7.8 μg/ml, and antiviral activity against herpes type 2 at 25 μg/ml.

EXAMPLE 84

2-(2-Dimethylaminoethoxy)-10-methyl-9-(3-fluorobenzyl)acridinium chloride hydrochloride [I; R is CH₂C₆H₄F-3, R' is CH₃, R" is H, —O—Y—N=Z is 2-O-CH₂CH₂N(CH₃)₂, An is Cl], dihydrate, light brown powder, m.p. 207°-211° C.(dec.). This compound was completely effective orally in the curative test against a murine infection with *T. brucei* at a dose level of 200 mg/kg/day×4; and showed bacteriostatic activity against *S. aureus* and *S. pyogenes* at MIC 15.6 μg/ml.

EXAMPLE 85

2-(2-Diethylaminoethoxy)-10-methyl-9-benzylacridinium chloride hydrochloride [I; R is CH₂C₆H₅, R' is CH₃, R" is H, —O—Y—N=Z is 2-O-CH₂CH₂N(C₂H₅)₂, An is Cl], monohydrate, yellow powder, m.p. 103°-107° C. This compound was completely effective orally in the curative test against a murine infection with *T. brucei* at a dose level of 100 mg/kg/day×4; and showed bacteriostatic activity against *S. aureus* and *S. pyogenes* at MIC 31.3 μg/ml.

EXAMPLE 86

2-(2-Dimethylaminoethoxy)-6-chloro-10-methyl-9-benzylacridinium chloride hydrochloride [I; R is CH₂C₆H₅, R' is CH₃, R" is 6-Cl, —O—Y—N=Z is 2-O-CH₂CH₂N(CH₃)₂, An is Cl], monohydrate, orange crystals, m.p. 200°-208° C.(dec.). This compound in the oral curative test against a murine infection with *T. brucei* was toxic to the animals at 200 mg/kg/day×4 and ineffective at 50 mg/kg/day×4. It showed bacteriostatic and fungistatic activity against *S. pyogenes*, *C. albicans* and *T. mentagrophytes* at MIC 7.8 μg/ml, 15.6 μg/ml and 31.3 μg/ml, respectively; and had antiviral activity against herpes type 2 at 12 μg/ml.

EXAMPLE 87

3-(2-Dimethylaminoethoxy)-7-methoxy-10-methyl-9-benzylacridinium chloride hydrochloride [I; R is CH₂C₆H₅, R' is CH₃, R" is 7-CH₃O, —O—Y—N=Z is 3-O-CH₂CH₂N(CH₃)₂, An is Cl], hydrate, m.p. 180°-183° C.(dec.), orange crystals. This compound was ineffective against *T. brucei* at a dose level of 200 mg/kg/day×4 but showed antiviral activity in vitro against herpes simplex virus type 2 at a concentration of 12 micrograms per milliliter.

EXAMPLE 88

3-(2-Diethylaminoethoxy)-7-methoxy-10-methyl-9-benzylacridinium chloride hydrochloride [I; R is CH₂C₆H₅, R' is CH₃, R" is 7-CH₃O, —O—Y—N=Z is 3-O-CH₂-CH₂N(C₂H₅)₂, An is Cl], hydrate, m.p. 196°-200° C.(dec.), orange powder.

EXAMPLE 89

1-(2-Dimethylaminoethoxy)-10-methyl-9-benzylacridinium chloride dihydrochloride [I; R is CH₂C₆H₅, R' is CH₃, R" is H, —O—Y—N=Z is 1-O-CH₂CH₂N(CH₃)₂], hydrate, m.p. 114°-128° C., red crystals.

I claim:

1. A pharmaceutically acceptable acid-addition salt of a compound of the formula

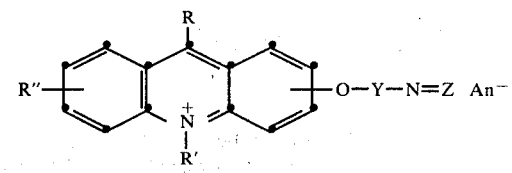

wherein R is phenyl, benzyl, or phenyl or benzyl substituted by a single substituent selected from the group consisting of lower-alkyl, lower-alkoxy or halogen; R' is lower-alkyl or benzyl; R" is hydrogen, chloro or lower-alkoxy; —Y—N=Z together is 9-methylgranatanin-3-yl; and An⁻ is a pharmaceutically acceptable anion.

2. A compound of the formula

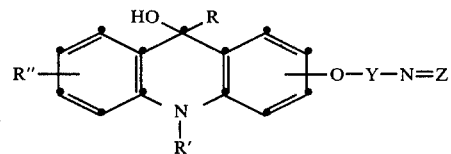

wherein R is phenyl, benzyl, or phenyl or benzyl substituted by a single substituent selected from the group consisting of lower-alkyl, lower-alkoxy or halogen; R' is lower-alkyl or benzyl; R" is hydrogen, chloro or lower-alkoxy; —Y—N=Z together is 9-methylgranatanin-3-yl; or a lower-alkyl halide or R°-sulfonate quaternary ammonium salt thereof wherein R° is lower-alkyl or aralkyl.

3. A compound according to claim 2 wherein R is phenyl or substituted phenyl.

4. exo-3-(9-Methylgranatanin-3-yloxy)-9,10-dihydro-10-methyl-9-phenyl-9-acridinol, according to claim 3.

5. exo-1-(9-Methylgranatanin-3-yloxy)-9,10-dihydro-10-methyl-9-phenyl-9-acridinol, according to claim 3.

6. A compound of the formula

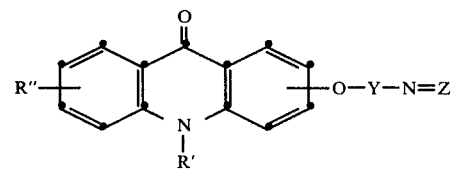

wherein R' is lower-alkyl or benzyl; R" is hydrogen, chloro or lower-alkoxy; —Y—N=Z together is 9-methylgranatanin-3-yl; or a pharmaceutically acceptable acid-addition salt thereof.

7. exo-1-(9-Methylgranatanin-3-yloxy)-10-methyl-9(10H)-acridinone, according to claim 6.

8. A method for combatting viruses which comprises contacting the locus of said viruses with a composition containing an antivirally effective amount of at least one compound of the formula

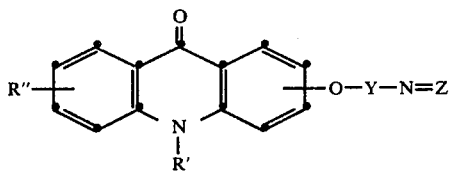

wherein R' is lower-alkyl or benzyl; R" is hydrogen, chloro or lower-alkoxy; Y is lower-alkylene of from two to four carbon atoms wherein the terminal valences are on separate carbon atoms; N=Z is di-lower-alkylamino, piperidino, pyrrolidino, morpholino or N-methylpiperazino; or Y—N=Z together is 9-methylgranatanin-3-yl; or a pharmaceutically acceptable acid-addition salt thereof; in admixture with a suitable carrier or diluent.

9. A method for combatting viruses which comprises contacting the locus of said viruses with a composition containing an antivirally effective amount of 1-(2-dimethylaminoethoxy)-10-methyl-9(10H)-acridinone or a pharmaceutically acceptable acid-addition salt thereof in admixture with a suitable carrier or diluent.

10. exo-3-(9-Methylgranatanin-3-yloxy)-10-methyl-9(10H)-acridinone.

* * * * *

UNITED STATES PATENT AND TRADEMARK OFFICE
CERTIFICATE OF CORRECTION

PATENT NO. : 4,244,954
DATED : January 13, 1981
INVENTOR(S) : John W. Schulenberg It is certified that error appears in the above—identified patent and that said Letters Patent are hereby corrected as shown below:

Column 12, line 42, "1-O(CH$_2$)$_3$N(C$_3$)$_2$" should read --1-O(CH$_2$)$_3$N(CH$_3$)$_2$--; line 59, "R;40" should read --R'--; line 65, "R' is CHHd" should read --R' is CH$_3$,--; line 66, delete "3," at beginning of line.

Column 13, line 11, delete entire line and insert --$_3$OC$_6$H$_4$, R' is CH$_3$, R" is H, -O-Y-N=Z is--; line 13, "8;b 33" should read --(33--; line 15, "(0.4 m.)" should read --(0.04 m.)--; line 40, "4-O-$_2$CH$_2$N(CH$_3$)$_2$" should read --4-O-CH$_2$CH$_2$N(CH$_3$)$_2$--.

Column 14, line 51, "-O;13 Y-N=Z" should read -- -O-Y-N=Z--.

Column 16, line 25, "100 1 mg/kg." should read --100 mg/kg.--; line 36, "S. pyrogenes" should read --*S. pyrogenes*--.

Signed and Sealed this

Twenty-first Day of July 1981

[SEAL]

Attest:

GERALD J. MOSSINGHOFF

Attesting Officer  Commissioner of Patents and Trademarks